United States Patent [19]
Tardi et al.

[11] Patent Number: 5,780,054
[45] Date of Patent: Jul. 14, 1998

[54] METHODS FOR INCREASING THE CIRCULATION HALF-LIFE OF PROTEIN-BASED THERAPEUTICS

[75] Inventors: Paul G. Tardi, Richmond; Erik Swartz, Vancouver; Marcel B. Bally, Bowen Island; Pieter R. Cullis, Vancouver, all of Canada

[73] Assignee: University of British Columbia, Canada

[21] Appl. No.: 588,014

[22] Filed: Jan. 17, 1996

[51] Int. Cl.$^6$ .................................................. A61K 9/127
[52] U.S. Cl. .................................................. 424/450; 436/829
[58] Field of Search .................................. 424/450; 436/829; 935/54

[56] References Cited

U.S. PATENT DOCUMENTS 5,447,722  9/1995  Lang ............................... 424/280.1

OTHER PUBLICATIONS

Perrin, Vaccine 3, p. 325 Sep. 1985.
Park BBA 1108 pp. 257–260, 1992.
Allen, TiPS 15:215 (1994).
Bally, et al., Cancer Chemother. Pharmacol. 27:13 (1990).
Bally, et al., Biochim. Biophys. Acta 1023:133 (1990).
Bally, et al., Liposome Technology: 2nd edition, vol. 3. G. Gregoriadis, ed. CRC Press, Inc., p. 27.
Brewer et al., Clin. Exp. Immunol. 97:164 (1994).
Derksen, et al., Biochim. Biophys. Acta 931:33.
Dillman, Antibody Immunocon. Radiopharm. 3:1 (1990).
Harasym, et al., Bioconjugate Chem. 6:187 (1995).
Hope, et al., Biochim. Biophys. Acta 812:55.
Jain, Sci. Am. 271:58 (1994).
Khazaeli, et al., J. Immunother. 15:42 (1994).
Ledermann, et al., Br. J. Cancer 58:654 (1988).
Longman, et al., J. Pharm. Exp. Therm. (in press).
Longman, et al., Cancer Chemother Pharmacol 36:91–101.
Loughrey, et al., J. Immun. Methods 132:25–35 (1990).
Mayer, et al., J. Liposome Res. 1:463 (1990).
Mayer, et al., Biochim. Biophys. Acta 817:193.
Mayer, et al., Biochim. Biophys. Acta 851:123.
Mayer, et al., Biochim Biophys. Acta 1025:143.
Parr et al., Biochim. Biophys. Acta 1168:249 (1993).
Parr, et al., Biochim. Biophys. Acta 1195:21 (1994).
Phillips, et al., J. Immunol. 152:3168 (1994).
Pinnaduwage, et al., Biochemistry 31:2850–2855 (1992).
Rahman, et al., Br. J. Cancer 54:401 (1986).
Sands, Cancer Res. [Suppl.] 50:809s (1990).
Shockley, et al., Cancer Res. 52:367 (1992).
Vidal, et al., Clin. Exp. Allergy 23:15 (1993).
Vitetta et al., Cancer Res. 54:5301 (1994).
Weinstein, et al. Cancer Res. [Suppl.] 52:2747s (1992).
Woodle, et al., Bioconjugate Chem. 5:493–496 (1994).
Yuan, et al., Cancer Res. 54:3352 (1994).

Primary Examiner—Gollamudi S. Kishore
Attorney, Agent, or Firm—Townsend and Townsend and Crew LLP

[57] ABSTRACT

Methods of increasing the circulation half-life of protein-based therapeutics in a host, the methods comprising: (a) administering to the host an amount of a first liposome formulation comprising liposomes and an antineoplastic agent; and (b) administering to the host a second formulation comprising the protein-based therapeutic, wherein the amount of the first liposome formulation is sufficient to suppress an immune response to the protein-based therapeutic of the second formulation, thereby increasing the circulation half-life of the protein-based therapeutic.

14 Claims, 5 Drawing Sheets

METHODS FOR INCREASING THE CIRCULATION HALF-LIFE OF PROTEIN-BASED THERAPEUTICS

BACKGROUND OF THE INVENTION

Although it is unlikely that monoclonal antibody based anti-cancer pharmaceuticals will become useful for first-line treatment of solid tumors, it is evident that the specificity achieved through the use of antibodies will be of therapeutic value in an adjuvant setting (see Vitetta, et al., *Cancer Res.* 54:5301 (1994) and Shockley, et al., *Cancer Res.* 52:367 (1992)). Advancement of this technology is hindered, however, by the fact that following initial treatment, immune responses to administered antibodies restricts further applications. Specifically, generation of heterologous antibodies leads to rapid elimination of the therapeutic antibody and significantly reduces in vivo targeting efficiency (see, Dillman, *Antibody Immunocon. Radiopharm.* 3:1 (1990)). HAMA, or human anti-mouse antibody, responses can be minimized through use of humanized murine antibodies, however production of anti-idiotypic antibodies is still observed (see, Khazaeli, et al., *J. Immunother.* 15:42 (1994)). Alternatively, immunosuppressive agents may be used to prevent an immune response against a therapeutic monoclonal antibody (see, Ledermann, et al., *Br. J. Cancer* 58:654 (1988)).

Despite the fact that monoclonal antibodies exhibit exquisite specificity, typically less than 0.1% of the injected protein (per gram tumor) accumulates in the target tumor following intravenous administration of a tumor specific monoclonal antibody (see, Sands, *Cancer Res.* [Suppl.] 50:809s (1990)). For this reason, methods utilizing antibodies for drug delivery, should engineer antibodies to deliver as much of the therapeutic agent as possible. Researchers working in the area of liposome and polymer drug delivery systems utilize this rationale to promote development of antibody targeted macromolecular drug carriers (see, Allen, *TIPS* 15:215 (1994)). The primary criticism of such a rationale is that attachment of antibodies to liposomes, for example, will significantly reduce the tendency for the antibody to localize within the target site. This is anticipated based on studies demonstrating that access of macromolecules to tumors is restricted due to the barriers provide by the tumor vasculature (see Shockley, et al., *Cancer Res.* 52:367 (1992) and Weinstein, et al., *Cancer Res.* [Suppl.] 52:2747s (1992)) as well as the presence of interstitial pressure within the tumor (Jain, *Sci. Am.* 271:58 (1994)). Attaching a relatively small targeting ligand, that already exhibits restricted access to extravascular sites, to a large carrier system, such as a liposome, will only serve to further reduce targeting efficiencies.

Paradoxically one of the primary benefits for utilizing liposomal drug carrier systems is their enhanced drug delivery to sites of tumor growth. Studies have demonstrated that increased tumor accumulation of drugs is achieved as a consequence of carrier mediated changes in drug pharmacokinetic behavior (Mayer, et al., *J. Liposome Res.* 1:463 (1990)). In particular, increases in tumor delivery have been correlated with the tendency of liposomes, to escape the tumor blood vasculature (Yuan, et al., *Cancer Res.* 54:3352 (1994)). The biological processes regulating extravasation are not well understood. Regardless, studies using murine tumor models indicate that from 1 to 5% of the injected drug dose (per gram tumor) can be achieved following i.v. administration of liposomal carriers, provided the liposomes are designed for optimal circulation lifetimes (see Longman, et al., *J. Pharm. Exp. Ther.* (in press)). Based on these observations, present drug delivery strategies focus on the design of targeted liposomal carriers that exhibit: i) enhanced circulation lifetimes; ii) tendency to accumulate within extravascular sites associated with tumors and iii) optimal binding to target cell populations. The principle objective of such research is to facilitate a redistribution of regionally localized liposomes such that liposomes within an interstitial compartment bind efficiently to defined target cell populations.

Enhancing the circulation lifetimes for liposomal drug delivery systems can be envisaged as arising from either reducing "non-specific" clearance of liposomes or by reducing their "specific" clearance. Non-specific clearance is typically thought to occur through interactions with Kupffer cells which are associated with the liver, whereas specific clearance typically occurs via generation of antibodies to proteins which are either components of a liposome targeting system or are drug carriers themselves.

As a result, any strategy considering therapeutic applications of targeted liposomal carriers must still contend with the serious potential for the generation of an immune response against to surface associated proteins. Others have demonstrated, in immune competent animals, that antibody-coated liposomes are highly immunogenic (Phillips, et al., *J. Immunol.* 152:3168 (1994)). Immunogenicity effects significantly reduce circulation lifetimes and cause decreases in targeting efficiency. It is important, however, to consider whether the immune response to protein-coated liposomes is a significant concern when the liposomes are being utilized for the delivery of cytotoxic anticancer drugs, such as doxorubicin. Macrophage are known to play an important role in the generation of an immune response to foreign proteins (see, Vidal, et al., *Clin. Exp. Allergy* 23:15 (1993) and Brewer, et al., *Clin. Exp. Immunol.* 97:164 (1994)). Liposomal doxorubicin, in the absence of associated targeting ligands, is a potent immune suppressant (see, Rahman, et al., *Br. J. Cancer* 54:401 (1986)). This activity is reflected by extended suppression of spleen and bone marrow cellularity (see, Bally, et al., *Cancer Chemother. Pharmacol.* 27:13 (1990)) as well as a prolonged inhibition of RES phagocytic capacity (Parr, et al., *Biochim. Biophys. Acta* 1168:249 (1993)). The latter leads to significant increases in circulation lifetimes for the liposomal carrier and significant decreases in liposome accumulation in the liver.

The present invention arises from the surprising discovery that liposomal formulations of doxorubicin, when administered to a mammal, can eliminate an immune response to a subsequently administered protein, protein-based carrier, or other macromolecular drug carrier having a surface-associated targeting protein.

SUMMARY OF THE INVENTION

The present invention provides a method of increasing the circulation half-life of protein-based therapeutics in a host, the method comprising:

(a) administering to the host an amount of a first formulation comprising liposomes and an antineoplastic agent; and (b) administering to the host a second formulation comprising the proteinbased therapeutics, wherein the amount of the first formulation is sufficient to suppress an immune response to the protein-based therapeutics of the second formulation, thereby increasing the circulation half-life of the protein-based therapeutics.

DETAILED DESCRIPTION OF THE INVENTION

Abbreviations and Definitions

Abbreviations used herein have the following meanings: i.v., intravenous; RES, reticuloendothelial system; SPDP, N-succinimidyl 3-(2-pyridyldithio) propionic acid; DTT, dithiothreitol; NEM, N-ethylmaleimide; MPB-DPPE, N-(4-(P-maleimidophenyl)butyryl) dipalmitoyl-phosphatidylethanolamine; QELS, quasielastic light scattering; Chol, cholesterol; DMPC, 1,2-dimyristoylphosphatidylcholine; DSPC, 1,2-distearoylphosphatidylcholine; EDTA, ethylenediaminetetraacetic acid; HEPES, N-(2-hydroxyethyl)piperidine-N'-2-ethanesulphonic acid; HBS, HEPES buffered saline; MLV, multilammelar vesicles; PEG-DSPE, poly(ethylene glycol)-modified distearoylphosphatidylethanolamine; LUV, large unilamellar vesicles; PEG, poly(ethylene glycol); ³H-CHE, ³H-cholesteryl hexadecyl ether.

The term "protein" refers to a polypeptide or polyaminoacid which can be either naturally occurring or synthetic. As used herein, the term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

As used herein the term "antibody" includes the various forms above, as well as single chain forms, which have present a carbohydrate group which can be oxidized for use in the present invention and which when oxidized will not interfere with antigenic recognition. Methods of producing antibodies suitable for use in the present invention are well known to those skilled in the art and can be found described in such publications as Harlow & Lane, *Antibodies: A Laboratory Manual*, Cold Spring Harbor Laboratory, (1988).

"Monoclonal antibodies" may be obtained by various techniques familiar to those skilled in the art. Briefly, spleen cells from an animal immunized with a desired antigen are immortalized, commonly by fusion with a myeloma cell (see, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

As used herein, the term "host" refers to a human, rat, mouse, dog, cow, sheep, horse, cat and goat.

Description of the Embodiments

The present invention derives from the surprising discovery that a liposomal formulation of an antineoplastic agent can suppress an immune response to a protein-based therapeutic.

Thus, in one aspect, the present invention provides a method of increasing the circulation half-life of protein-based therapeutics in a host, the method comprising:

(a) administering to the host an amount of a first formulation comprising liposomes and an antineoplastic agent; and (b) administering to the host a second formulation comprising protein-based therapeutics, wherein the amount of the first formulation is sufficient to suppress an immune response to the protein-based therapeutics of the second formulation, thereby increasing the circulation half-life of the protein-based therapeutics.

In this aspect of the invention, a first formulation of liposomes and an antineoplastic agent is administered to a host. The liposomes of the first formulation will preferably encapsulate the antineoplastic agent, in an amount which is sufficient to suppress an immune response to a protein-based therapeutic. The effective amount of the antineoplastic agent is in the range of from about 0.01 mg/kg to about 100 mg/kg of body weight of the animal. The precise amount of the antineoplastic agent will be determined by such factors as the particular agent and the type of host. Additionally, the amount of the antineoplastic agent to be administered in the first formulation will depend on the clinical condition of the patient (or host), the side effects and the stability of the agent in the formulation. Thus, the physician or veterinarian will employ the appropriate preparation containing the appropriate concentration of the antineoplastic agent in the liposome formulation, as well as the amount of formulation administered, depending upon clinical experience with the patient in question or with similar patients.

A number of antineoplastic agents are useful in the present invention including doxorubicin, bleomycin, vinblastine, vincristine, etoposide and etoposide phosphate, paclitaxel, teniposide, daunomycin, melphalan, cyclophosphamide, chlorambucil, cisplatin, carboplatin, methotrexate, podophyllotoxin, verrucarin A, anguidine, mechlorethamine, leucovorin, cytosine or adenine arabinosides, 1-(2-deoxy-2-fluoro-β-D-arabinofuranosyl)-5-iodocytosine, 5-iodo-5'-amino-2',5-dideoxyuridine, 5'-amino-5'-deoxythymidine, mitomycin, 1-amantanamine, rimantadine and tamoxifen.

For formulations which contain doxorubicin, the preferred amount of doxorubicin is from about 2 to about 12 mg/kg for use in mice, and from about 0.07 to about 7.0 mg/kg in humans. More preferably, the amount of doxorubicin is from about 0.3 to 1.0 mg/kg in humans.

The liposomes which are present in this first formulation can be any of a variety of liposomes which are typically used in pharmaceutical preparations. These liposomes are typically formed from standard vesicle-forming lipids, which generally include neutral and charged phospholipids and a sterol, such as cholesterol. The selection of lipids is generally guided by consideration of, e.g., liposome size and stability of the liposomes in the bloodstream.

Typically, the major lipid component in the liposomes is phosphatidylcholine. Phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Phosphatidylcholines containing saturated fatty acids with carbon chain lengths in the range of $C_{14}$ to $C_{22}$ are preferred. Phosphatidylcholines with mono or diunsaturated fatty acids and mixtures of saturated and unsaturated fatty acids may also be used. Liposomes useful in the present invention may also be composed of sphingomyelin or phospholipids with head groups other than choline, such as ethanolamine, serine, glycerol and inositol. In particular, phospholipids suitable for formation of liposomes useful in the methods and compositions of the present invention include, e.g., phosphatidylcholine, phosphatidylglycerol, lecithin, β,γ-dipalmitoyl-α-lecithin, sphingomyelin, phosphatidylserine, phosphatidic acid, N-(2, 3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, and the like. Non-phosphorus containing lipids may also be used in the liposomes used in the present invention. These include, e.g., stearylamine, dodecylamine, acetyl palmitate, fatty acid amides, and the like. Additional lipids suitable for use in the liposomes of the present invention are well known to persons of skill in the art and are cited in a variety of well known sources, e.g., *McCutcheon's Detergents and Emulsifiers and McCutcheon's Functional Materials*, Allured Publishing Co., Ridgewood, N.J., both of which are incorporated herein by reference. Preferred liposomes will include a sterol, preferably cholesterol, at molar ratios of from 0.1 to 1.0 (cholesterol:phospholipid). Most preferred liposome compositions are distearoylphosphatidylcholine/cholesterol, dipalmitoylphosphatidylcholine/cholesterol, and sphingomyelin/cholesterol.

A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,946,787, PCT Publication No. WO 91/17424, Deamer and Bangham, *Biochim. Biophys. Acta*, 443:629–634 (1976); Fraley, et al., *Proc. Natl. Acad. Sci. USA*, 76:3348–3352 (1979); Hope, et al., *Biochim. Biophys. Acta*, 812:55–65 (1985); Mayer, et al., *Biochim. Biophys. Acta*, 858:161–168 (1986); Williams, et al., *Proc. Natl. Acad. Sci.*, 85:242–246 (1988), the text *Liposomes*, Marc J.Ostro, ed., Marcel Dekker, Inc., New York, 1983, Chapter 1, and Hope, et al., *Chem. Phys. Lip.* 40:89 (1986), all of which are incorporated herein by reference. Suitable methods include, e.g., sonication, extrusion, high pressure/homogenization, microfluidization, detergent dialysis, calcium-induced fusion of small liposome vesicles, and ether-infusion methods, all well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Unilamellar vesicles are generally prepared by sonication or extrusion. Sonication is generally performed with a tip sonifier, such as a Branson tip sonifier, in an ice bath. Typically, the suspension is subjected to several sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass.

Following liposome preparation, the liposomes which have not been sized during formation may be sized to achieve a desired size range and relatively narrow distribution of liposome sizes. A size range of about 0.05–0.2 microns allows the liposome suspension to be sterilized by filtration through a conventional filter, typically a 0.1 micron filter. The filter sterilization method can be carried out on a high throughput basis if the liposomes have been sized down to about 0.1–0.2 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.*, 10:421–450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present invention, liposomes having a size of from about 0.05 microns to about 0.15 microns are preferred.

The liposomes which are part of the first formulation will, in some embodiments, have an attached protein and are referred to herein as "protein-liposome conjugates." When protein-liposome conjugates are used in the first formulation, they can be prepared by incorporating the protein into the liposomes by a variety of techniques well known to those of skill in the art. See, for example, Loughrey, et al., *J. Immun. Methods* 132:25–35 (1990); Pinnaduwage, et al., *Biochemistry* 31:2850–2855 (1992); and Heath, METHODS IN ENZYMOLOGY, Green, et al., eds., vol. 149, pp. 111–119 (1987). In one example, a protein can be modified with the amine reactive agent, N-succinimidyl 3-(2-pyridyldithio) propionic acid (SPDP) by incubating SPDP with the protein at room temperature for 10 min. using at least a 10-fold molar excess of SPDP. The SPDP-modified protein is then reduced with dithiothreitol (DTT) and passed down a SEPHADEX® G-50 column to remove unreacted SPDP and DTT. The extent of modification of the protein may be determined by estimating the concentration of the protein at 280 nm (molar extinction coefficient, $E_{280}$: $1.66 \times 10^5$) prior to the addition of DTT, and the 2-thiopyridine concentration may be measured at 343 nm ($E_{343}$: 7550) 10 min after addition of DTT.

The coupling of SPDP-modified protein to liposomes is then performed by incubating the liposomes with the protein derivative. The coupling reaction can be stopped by the addition of dithiothreitol (DTT) followed by the addition of N-ethyl maleimide (NEM). Unassociated protein can then be removed by gel filtration on SEPHAROSE® CL-4B equilibrated with HBS. In the absence of PEG-PE incorporation, crosslinking of vesicles during coupling can result in liposome aggregation (300–400 nm in diameter as determined by QELS). In some cases, aggregated protein-liposome conjugates can be re-extruded through stacked polycarbonate filters (100 nm pore size) to generate a defined size population, (130–170 nm in diameter).

As further noted above, the liposomes of the first formulation will preferably encapsulate doxorubicin. Incorporation of doxorubicin into a liposome can be carried out by any of a variety of methods known to those of skill in the art. The most common methods include encapsulation during liposome formation and the transmembrane potential loading method. In the encapsulation technique, doxorubicin is placed into the buffer from which the liposomes are made. The latter method has been described in detail in U.S. Pat. No. 4,885,172, U.S. Pat. No. 5,059,421, and U.S. Pat. No. 5,171,578, the contents of which are incorporated herein by reference.

Briefly, the transmembrane potential loading method can be used with essentially any conventional drug (in the case of the first formulation, doxorubicin) which can exist in a charged state when dissolved in an appropriate aqueous medium. A transmembrane potential is created across the bilayers of the liposomes or protein liposome conjugates and the drug is loaded into the liposome by means of the transmembrane potential. The transmembrane potential is generated by creating a concentration gradient for one or more charged species (e.g., $Na^+$, $K^+$ and/or $H^+$) across the membranes. This concentration gradient is generated by producing liposomes or protein liposome conjugates having different internal and external media. Thus, for a drug such as doxorubicin which is positively charged when ionized, a transmembrane potential is created across the membranes which has an inside potential which is negative relative to the outside potential, while for a drug which is negatively charged, the opposite orientation is used. In a particularly preferred embodiment, doxorubicin is loaded into the liposomes of the first formulation using a $H^+$ ion gradient (or pH gradient).

The second formulation used in the present invention comprises protein-based therapeutics. A number of protein-based therapeutics are contemplated as being within the scope of the present invention. As used herein, the term "protein-based therapeutics" refers to therapeutic agents which are proteins or polypeptides, as well as therapeutic compositions in which a protein works as a carrier or targeting agent. Examples of protein-based therapeutics include protein-coated liposomes (including those liposomes having a viral protein coating), peptide-containing liposomes, antibody-toxin conjugates, transferrin DNA bound to polylysine, and prodrugs having a protein-targeting group. The protein-coated liposomes are preferably antibody-coated liposomes in which the antibody is specific for an antigen associated with a target tissue.

As with the first formulations above, the protein used in the protein-coated liposomes of the present inventive method can be any of a variety of proteins, including antibodies (i.e., immunoglobulins such as IgG, IgA, IgD, IgM and IgE), monoclonal antibodies, immunomodulators (i.e., IL-1 and IL-2), hemaglutinin or other fusogenic proteins, avidin, transferrin epidermal growth factor and tumor necrosis factor (TNF). Preferably, the protein will be an antibody which is generated either to an antigen present in a diseased or compromised tissue or to an antigen present on a cell surface such as a cancer cell. The proteins used in the present invention can be obtained from commercial sources, isolated from natural products, or prepared according to protocols known to those of skill in the art. In preferred embodiments the glycosylated proteins include IgG, anti-CD4 (available from CedarLane Laboratories, Hormby, Ontario, Canada), anti-CD8 (from CedarLane Laboratories), anti-ICAM-1 (available from R & D Systems, Inc., Minneapolis, Minn., USA), anti-ICAM-2, CC49, α-Erb-B2, α-CEA, and pancarcinoma antibodies, as well as proteins such as avidin.

Preparation of protein-coated liposomes can be accomplished by a number of techniques known to those of skill in the art. For example, proteins can be attached to liposomes using such linkers as SPDP (described above) or by employing methods described in co-pending applications Ser. Nos. 08/316,394 (filed Sep. 30, 1994), 08/418,696 (filed Apr. 7, 1995) and 08/536,396 (filed Sep. 29, 1995). In the latter preparative methods, a protein which is glycosylated, is oxidized using a mild oxidizing agent, then reacted with a hydrazine containing linking group. The linking group contains further functionality which can be reacted with a lipid or liposome to complete the covalent attachment of protein to lipid or liposome. Other methods for coating liposomes with proteins are known to those of skill in the art and have been noted and referenced above.

In one group of preferred embodiments, the second formulation is a protein-coated liposome which further comprises an encapsulated therapeutic agent. The therapeutic agents used in this aspect of the present invention can be any of a variety of drugs which are selected to be an appropriate treatment for the disease to be treated in the target tissue. Often the drug will be an antineoplastic agent, such as vincristine, doxorubicin, cisplatin, bleomycin, cyclophosphamide, methotrexate, streptozotocin, and the like. It may also be desirable to deliver anti-infective agents to specific tissues by the present methods. The present inventive method can also be used for the selective delivery of other drugs including, but not limited to local anesthetics, e.g., dibucaine and chlorpromazine; beta-adrenergic blockers, e.g., propranolol, timolol and labetolol; antihypertensive agents, e.g., clonidine and hydralazine; anti-depressants, e.g., imipramine, amitriptyline and doxepim; anti-convelsants, e.g., phenytoin; antihistamines, e.g., diphenhydramine, chlorphenirimine and promethazine; antibacterial agents, e.g., gentamicin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents. Other particular drugs which can be used in the present invention are well known to those of skill in the art. Additionally, two or more therapeutic agents can be administered simultaneously if desired, where such agents produce complementary or synergistic effects.

The methods of loading conventional drugs into liposomes are well known to those of skill in the art, and have been discussed with respect to doxorubicin loading, above.

In some embodiments, it is preferred to include polyethylene glycol-(PEG), "PEG-like" compounds (e.g., poly(2-methyl-2-oxazoline) or poly(2-ethyl-2-oxazoline), see Woodle, et al., *Bioconjugate Chem.* 5:493–496 (1994)) or ganglioside $G_{M1}$-modified lipids to the liposomes which are part of the first formulation, the second formulation or both formulations. Addition of such components prevent liposome aggregation during coupling of the protein to the liposome. This also provides a means for increasing circulation lifetime and increasing the delivery of liposomes to the target tissues. Typically, the concentration of the PEG- or $G_{M1}$-modified lipids in the liposome membrane will be about 1–5%.

The liposome formulations of the present invention may be dehydrated using standard freeze-drying techniques, to extend their useful life. The liposomes and protein-liposome conjugates (including the protein-coated liposomes) can be frozen in liquid nitrogen prior to being dehydrated. Alternatively, the liposomes and protein-coated liposomes can be dehydrated without prior freezing by exposing the solutions of the liposomes to reduced pressures. When dehydration is carried out without prior freezing, it is preferred to include a protective sugar in the preparation. A variety of sugars can be used such as trehalose, maltose, sucrose, glucose, lactose, and dextran. In general, disaccharide sugars have been found to work better than monosaccharide sugars, with the disaccharide sugars trehalose and sucrose being the most effective.

Once the liposomes have been dehydrated, they can be stored for extended periods of time until they are to be used. When the dehydrated liposomes are to be used, rehydration is accomplished by simply adding an aqueous solution, e.g., distilled water, to the liposomes and allowing them to rehydrate.

If a drug is to be administered as part of the second formulation and is incorporated into protein-coated liposomes prior to dehydration, and no further composition changes are desired, the rehydrated conjugates can be used directly in therapy following known procedures described herein. In other instances, the drug will be added to the protein-coated liposomes just prior to use.

Pharmaceutical compositions comprising the liposomes of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of liposomes, in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, liposomes composed of irritating lipids may be diluted to low concentrations to lessen inflammation at the site of administration. For diagnosis, the amount of liposomes administered will depend upon the particular label used, the disease state being diagnosed and the judgement of the clinician but will generally be between about 0.01 and about 50 mg per kilogram of body weight, preferably between about 0.1 and about 5 mg/kg of body weight.

The liposomal formulations used in the present inventive method can be administered either simultaneously or, more preferably, sequentially. When the formulations are administered sequentially, the first formulation will preferably be administered first, followed by the second formulation.

The liposomal formulations can be administered parenterally, i.e., intraarticularly, intravenously, intraperitoneally, subcutaneously, or intramuscularly. More preferably, the formulations are administered intravenously or intraperitoneally by a bolus injection. Particular formulations which are suitable for this use are found in *Remington's Pharmaceutical Sciences*, Mack Publishing Company, Philadelphia, Pa., 17th ed. (1985).

The present invention also provides kits which include components for preparing the formulations used in the present inventive methods. The kit will typically be comprised of a container which is compartmentalized for holding the various elements of the kit. In one embodiment, one compartment will contain a second kit for loading doxorubicin into a liposome formulation just prior to use. Preferably, that liposome formulation will have an attached protein which is an antigen for a particular immune response for which suppression is desired. A second compartment will contain a protein-coated liposome formulation, preferably in an aqueous buffered solution. A third compartment, where necessary, will contain a drug which is to be loaded into the protein-coated liposomes. Alternatively, the protein-coated liposomes will have an encapsulated drug, as described above. In a preferred embodiment, freeze dried liposomes and protein-coated liposomes are provided along with appropriate buffers, doxorubicin and conventional drugs to prepare the liposome formulations used in the present inventive method.

The following examples are offered solely for the purposes of illustration, and are intended neither to limit nor to define the invention.

EXAMPLES

Materials 1,2-distearoyl-glycero-3-phosphocholine (DSPC) was purchased from Avanti Polar Lipids (Alabaster, Ala., USA). N-(4-(p-maleimidophenyl)butyryl)-dipalmitoyl phosphatidylethanolamine (MPB-DPPE) was obtained from Northern Lipids, Inc. (Vancouver, Canada). MePEG2000-S-DSPE (PEG-DSPE) was a generous gift obtained from Dr. S. Ansell and prepared as described elsewhere (Parr, et al., *Biochim. Biophys. Acta* 1195:21 (1994)). IMJECT® (ovalbumin) and N-succinimidyl 3-(2-pyridyldithio) propionate (SPDP) were obtained from Pierce (Rockford, Ill., USA). Cholesterol, N-(2-hydroxyethyl) piperazine-N'-(2-ethanesulphonic acid) (HEPES), SEPHAROSE® CL-4B, SEPHADEX® G-25, SEPHADEX® G-50 and dithiothreitol (DTT) were obtained from Sigma Chemical Co. (St. Louis, Mo., USA). $^3$H-Cholesteryl hexadecyl ether ($^3$H-CHE) was obtained from Amersham (Oakville, Ontario, Canada). Doxorubicin was obtained from Adria Laboratories, Inc. (Mississauga, Ontario, Canada). Freund's Complete and Incomplete Adjuvant was obtained from GIBCO (Grand Island, N.Y., USA). Female C3H/HeJ mice were obtained from the British Columbia Cancer Agency Joint Animal Facility breeding colony who obtain parental stock from Jackson Laboratories (CA).

Methods (a) Preparation of Liposomes

Large unilamellar vesicles were prepared according to the method of Hope et al. (see, Hope, et al., *Biochim. Biophys. Acta* 812:55 (1985)). Lipid mixtures consisting of 52% DSPC/45% cholesterol/2% PEG-DSPE/1% MPB-DPPE (mole ratio) and a small amount of $^3$H-cholesteryl hexadecyl ether were dissolved in chloroform. The solution was subsequently concentrated under a stream of nitrogen gas to produce a homogenous lipid film. The film was then placed under high vacuum for at least 4 hours before hydration at 65° C. with 300 mM citric acid (pH 4.0). The resulting lipid preparation (50 mM) was frozen and thawed 5 times (see, Mayer, et al., *Biochim. Biophys. Acta* 817:193 (1986)) prior to extrusion 10 times through three stacked 100 nm polycarbonate filters (Nuclepore) using an extrusion apparatus (Lipex Biomembranes, Inc.) set to 65° C. Liposome particle size was determined by quasielastic light scattering (QELS) measurements (using a Nicomp 370 particle sizer operating at a wavelength of 632.8 nm). The external buffer of the liposome suspension (citrate pH 4.0), was exchanged into HBS (25 mM HEPES, 150 mM NaCl, pH 7.5) by gel filtration on SEPHADEX® G-25.

(b) Coupling of Thiolated Ovalbumin to Liposomes

Imject® (ovalbumin) was modified with the amine reactive crosslinker SPDP according to procedures described previously (see Loughrey, et al., *J. Immunol. Methods* 132:25 (1990)). Briefly, an ovalbumin solution was prepared in 0.9% NaCl to 8 mg/mL. SPDP was dissolved in ethanol and then diluted into HBS just prior to ovalbumin modification. The reaction was carried out with a 5-fold molar excess of SPDP to ovalbumin at room temperature for 30 minutes. The ovalbumin was then passed down a SEPHADEX® G-50 column equilibrated with HBS to remove any unreacted SPDP. The ovalbumin was then reduced with DTT (25 mM for 30 min) and the thiolated product isolated by gel filtration on SEPHADEX® G-50 equilibrated with HBS. The modified ovalbumin was then incubated with liposomes (see section (a) for preparation of liposomes having a reactive functionality on the liposome surface (1% MPB)) at a ratio of 90 μg of protein per μmole lipid (15 mM final lipid concentration). The coupling reaction was carried out in HBS and stirred at room temperature for 18 hours. The resulting liposomes were then passed down a SEPHAROSE® CL-4B column equilibrated with HBS to remove any free ovalbumin. The amount of ovalbumin coupled to the liposomes was determined using the Pierce Micro BCA assay in the presence of 1% Triton X-100 to disrupt the liposomes. The reaction typically results in 30–40 μg of ovalbumin coupled per mmole lipid.

(c) Doxorubicin Encapsulation

Doxorubicin was encapsulated in selected preparations using the transmembrane pH gradient driven loading procedure as previously described (see, Mayer, et al., *Biochim. Biophys. Acta* 851:123 (1985)). Briefly, ovalbumin coated liposomes (pH 4.0 in/pH 7.5 out) and doxorubicin (solubilized in 0.9% NaCl) were pre-heated to 65° C. for 5 minutes prior to mixing. The liposomes were added to doxorubicin to achieve a drug-to-lipid ratio of 0.2:1 (mol/mol). This mixture was incubated for 10 min at 65° C. with intermittent mixing. Drug encapsulation efficiency was determined as described elsewhere (see, Mayer, et al., *Biochim. Biophys. Acta* 1025:143 (1990)) and the procedure typically resulted in entrapment efficiencies of >98%. In experiments where empty liposomes were used, the same procedure was followed with the exception that a solution of 0.9% NaCl was used to replace doxorubicin.

(d) In Vivo Clearance Studies

Groups of four C3H/HeJ mice per experimental point were given the specified treatment as a single i.v. dose via a lateral tail vein. The injection, given in a volume of 200 μL, contained 50 µg of ovalbumin. In animals receiving control (protein free) liposomes, the dose was chosen based on the lipid dose given for the ovalbumin-coated liposome group. This lipid dose was approximately 45 mg/kg. In the groups receiving doxorubicin, the drug dose was approximately 8 mg/kg. It should be noted that in mice, the maximum tolerated dose of doxorubicin encapsulated in DSPC/Chol liposomes is greater than 60 mg doxorubicin/kg.

Liposomal lipid was measured using the lipid marker $^3$H-cholesteryl hexadecyl ether. Previous studies have shown this lipid to be non-exchangeable and non-metabolizable (see, Dirksen, et al., *Biochim. Biophys. Acta* 931:33 (1987)). The circulating levels of injected liposomal lipid was determined 4 hours after i.v. injection. Blood (25 µL) was obtained via a nick of a lateral tail vein where the blood was collected into microcapillary tubes that had been rinsed with 200 mM EDTA. The blood was mixed with a solution of 200 mM EDTA and the capillary tube was rinsed several times. The total volume of the sample was adjusted to 225 µL. The sample was placed on ice until it was centrifuged (500 g). The pelleted blood cells were washed once with 200 µL of 200 mM EDTA and the supernatants were collected and mixed with 5 mL of PICO-FLUOR® 40 scintillation cocktail (Packard). The amount of radioactivity in each sample was determined using a Beckman LS3801 scintillation counter. It was assumed that the hematocrit of the mice was 48% (see Bally, et al., in LIPOSOME TECHNOLOGY: 2ND EDITION, vol. 3, G.Geogoriadis, ed., CRC Press, Boca Raton, Fla., p. 27) therefore each 25 µL of whole blood contained 13 µL of plasma.

One week after the third injection (week four) all four groups of mice were injected with freshly prepared ovalbumin-coated liposomes (without doxorubicin). All mice were injected at an ovalbumin dose of 50 µg per mouse. Whole blood was collected at 1 and 4 hours by the tail nick procedure described above. At 24 hours animals were asphyxiated by $CO_2$, blood was collected via cardiac puncture and placed into EDTA coated microtainers (Becton Dickenson). For this latter sample, plasma was prepared by centrifuging at 500 g for 10 min. Lipid levels in the plasma were determined as described above where the amount of radioactivity in 50 µL of plasma was measured.

(e) Immunization of C3H/HeJ Mice with Ovalbumin mixed with Freund's Adjuvant

Additional groups (4 mice per group) of animals were immunized with free IMJECT® ovalbumin mixed with Freund's adjuvant. Briefly, the ovalbumin was dissolved in 0.9% NaCl to achieve a concentration of 0.5 mg/mL. For the first immunization, this solution was emulsified with Freund's complete adjuvant. Subsequent immunizations used ovalbumin emulsified with Freund's incomplete adjuvant. The water-in-oil emulsions were injected i.p. such that each mouse received 50 µg of ovalbumin in 200 µL. The animals were immunized every week for three weeks and terminated on the fourth week for assessment of circulating anti-ovalbumin IgG levels. In order to determine whether liposomal doxorubicin effected the ability of these animals to generate an immune response, 4 groups were established: i) Freund's adjuvant mixed with saline (no ovalbumin); ii) Freund's adjuvant with ovalbumin; iii) Freund's adjuvant with ovalbumin and an i.v. dose of DSPC/Chol liposomes and iv) Freund's adjuvant with ovalbumin and an i.v. dose of doxorubicin encapsulated in DSPC/Chol liposomes. For the latter two groups, liposomes (without surface associated ovalbumin) were administered i.v at a lipid dose of 100 mg/kg, 4 hrs prior to administration of the ovalbumin Freund's mixture. When the liposomes contained doxorubicin, the drug dose was approximately 18 mg/kg.

(f) Elisa Assay of Mouse Serum

Microtitre plates (Flow Laboratories) were coated with 50 µL of 40 µg/mL ovalbumin and incubated at 4° C. overnight. The plates were washed twice (phosphate buffered saline containing 0.1% (vol/vol) TWEEN® 20) and then blocked with 2% bovine serum albumin (BSA) for 1 hour at 37° C. The plates were rinsed prior to addition of mouse plasma in a final volume of 100 µL (the extent to which the plasma was diluted depended on treatment group). After a 1 hour incubation the plates were washed three times and 100 µL of 0.5 µg/mL biotin labelled goat anti-mouse IgG (diluted in Hank's solution with 1% BSA) was added. The plates were incubated at room temperature for 30 min and washed 3 times prior to addition of 100 µL of 500 mU/mL of streptavidin-β-galactosidase (diluted in Hank's solution with 1% BSA). Plates were incubated at room temperature for 30 min, washed, and the amount of plate associated β-galactosidase was determined. Chlorophenol red-β-D-galactopyranoside (100 µL of a 2 mg/mL solution) in HBSS, plus 1% BSA was added to the plates and incubated at room temperature for 1 hour. The amount of chlorophenol red produced was determined by measuring absorbance at 570 nm on a TITERLIK® plate reader. Antibody levels were estimated on the basis of standard curves consisting of known quantities of a rabbit polyclonal anti-ovalbumin IgG (Cortex Biochemicals, Calif., USA). Controls consisted of undiluted plasma samples obtained from untreated C3H/HeJ mice.

EXAMPLE 1

This example shows the clearance behavior of ovalbumin coated liposomes.

Figure 1:
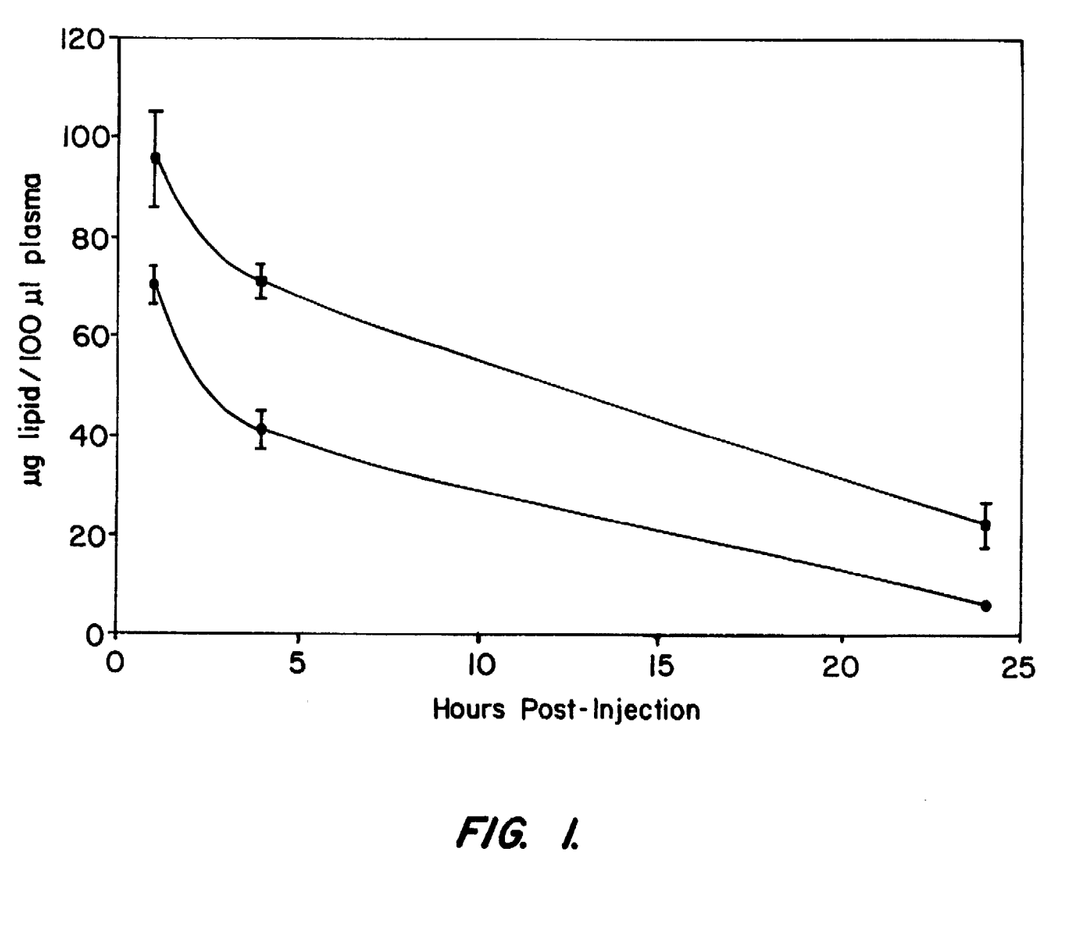
FIG. 1 illustrates the clearance of ovalbumin-coated PEG liposomes. Mice were injected i.v. with either 2% PEG liposomes (■) or ovalbumin-coated 2% PEG liposomes (●). Blood was collected at various time points and the amount of lipid remaining in the blood was determined. The results are plotted as an average of four separate experiments.

The plasma clearance behavior of liposomes with and without surface associated ovalbumin is shown in FIG. 1. These results, obtained following i.v. administration of liposomes at a lipid dose of approximately 45 mg/kg, suggest that liposomes with surface associated ovalbumin are eliminated from the circulation at a rate faster than that observed for control liposomes. One day following administration, for example, significantly higher levels of control liposomes (DSPC/Chol/MPB-PE/PEG-PE; 52:45:1:2 mole ratio) (approximately 20% of the injected lipid dose) can be found in the plasma compartment in comparison to identical liposomes with surface associated ovalbumin (less than 5% of the injected lipid dose). This result is consistent with previous studies showing that liposomes with surface associated proteins are cleared more rapidly than control liposomes following i.v. administration (see, Harasym, et al., *Bioconjugate Chem.* 6:187 (1995)). Protein mediated decreases in circulation lifetime is observed even under conditions where the size of the liposomes used are comparable.

EXAMPLE 2

This example illustrates the effect of repeated administration on plasma levels of ovalbumin liposomes with and without encapsulated doxorubicin.

Figure 2:
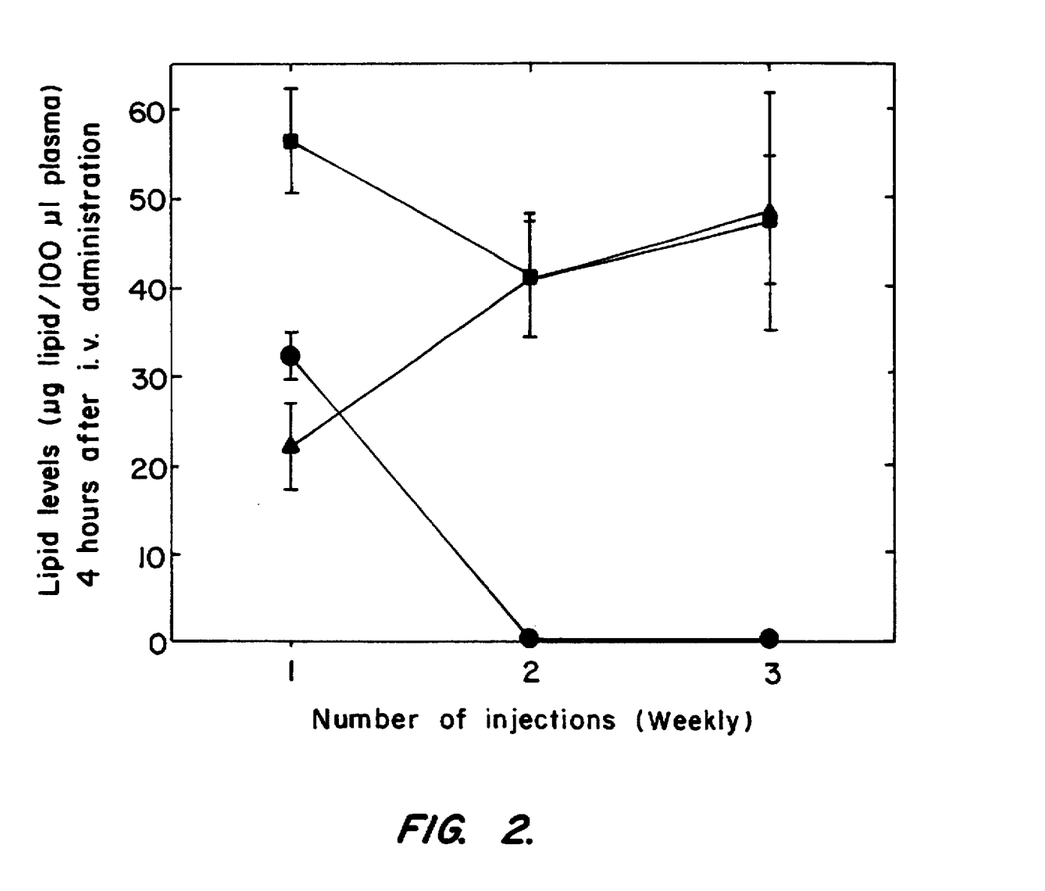
FIG. 2 shows the clearance of ovalbumin-coated PEG liposomes as a function of injection number. Mice were injected (i.v.) for three consecutive weeks with either 2% PEG liposomes (■), ovalbumin-coated 2% PEG liposomes (●) or ovalbumin-coated, doxorubicin loaded 2% PEG liposomes (▲). Four hours after injection blood was collected and the amount of lipid remaining in the blood was determined. The results are plotted as an average of four separate experiments.

Other studies have suggested that repeated administration of protein coated liposomes will elicit an immune response that decreases subsequent plasma circulation lifetimes (see, Phillips, et al., *J. Immunol.* 152:3168 (1994)). These results are confirmed here for ovalbumin liposomes (FIG. 2). Liposomes, either control liposomes or ovalbumin-coated PEG liposomes, were administered i.v. at weekly intervals for three weeks as described in the methods and plasma levels were determined 4 hr after each injection. Weekly injections of control liposomes, did not result in significant changes in circulating levels over the three week period. Four hours after the first injection there was 55 µg lipid/100 µL plasma, which corresponds to approximately 50% of the injected dose recovered in the blood compartment. Blood levels remained between 42 and 48 µg per 100 µL plasma after the second and third injections. As indicated in FIG. 1, when ovalbumin-coated PEG liposomes were administered, approximately 2 fold less lipid in comparison with protein free liposomes, is recovered after 4 hours. With the second injection this value decreased significantly, where less than 0.5% of the injected dose (>0.7 µg per 100 µL plasma) could be measured in the blood compartment This rapid clearance was also observed after the third injection. It should be noted that immediately after the third injection of ovalbumin liposomes the animals convulsed, exhibited labored breathing and adopted a hunched posture. After approximately 5 minutes the animals recovered, but remained inactive for periods in excess of one hour after administration. Animals receiving control (protein free) liposomes exhibited no changes in behavior after repeated liposome administration. However, when ovalbumin-coated PEG liposomes contained doxorubicin, the rapid clearance observed after the second injection did not occur (see FIG. 2). In fact the circulating levels observed at 4 hr after i.v. administration increased with each subsequent injection. After the third administration the levels of doxorubicin-loaded ovalbumin-coated PEG liposomes measured in the blood compartment were comparable to those obtained with control (no protein, no doxorubicin) liposomes. Approximately 50% of the injected dose of doxorubicin-loaded ovalbumin-coated PEG liposomes was found in the blood compartment at this time in comparison with less than 0.5% of the injected dose observed for ovalbumin-coated PEG liposomes in the absence of encapsulated drug.

EXAMPLE 3

This example illustrates the influence of liposomal doxorubicin on production of anti-ovalbumin antibodies.

Doxorubicin mediated increases in liposome circulation lifetimes have been reported in previous studies (see Bally, et al., *Biochim. Biophys. Acta* 1023:133 (1990)). It is believed that increased circulation lifetimes are due to the cytotoxic activity of encapsulated doxorubicin on phagocytic cells of the RES and, in particular, Kupffer cells residing in the liver (see Parr, et al., *Biochim. Biophys. Acta* 1168:249 (1993)). It is also well established that macrophages play a critical role in generation of immune responses (Vidal, et al., *Clin. Exp. Allergy* 23:15 (1993)) and, more specifically, are required for generation of IgG antibodies (Brewer, et al., *Clin. Exp. Immunol.* 97:164 (1994)). For this reason the influence of entrapped doxorubicin on generation of anti-ovalbumin antibodies was assessed and the results are summarized in FIG. 3. Plasma IgG levels were measured, using an ELISA assay, from C3H/HeJ mice given 3 weekly i.v. injections of control liposomes, free ovalbumin, ovalbumin-coated PEG liposomes or doxorubicin-loaded ovalbumin-coated PEG liposomes. The results were unambiguous. Anti-ovalbumin IgG was not detected in the plasma of mice receiving control liposomes or doxorubicin-loaded ovalbumin-coated PEG liposomes. In contrast, anti-ovalbumin IgG levels of 2.1 and 9.3 µg/mL plasma were obtained in animals immunized with free ovalbumin and ovalbumin-coated PEG liposomes, respectively. This result clearly indicates that generation of antibodies against liposome surface associated proteins can be inhibited by the presence of encapsulated doxorubicin.

Figure 4:
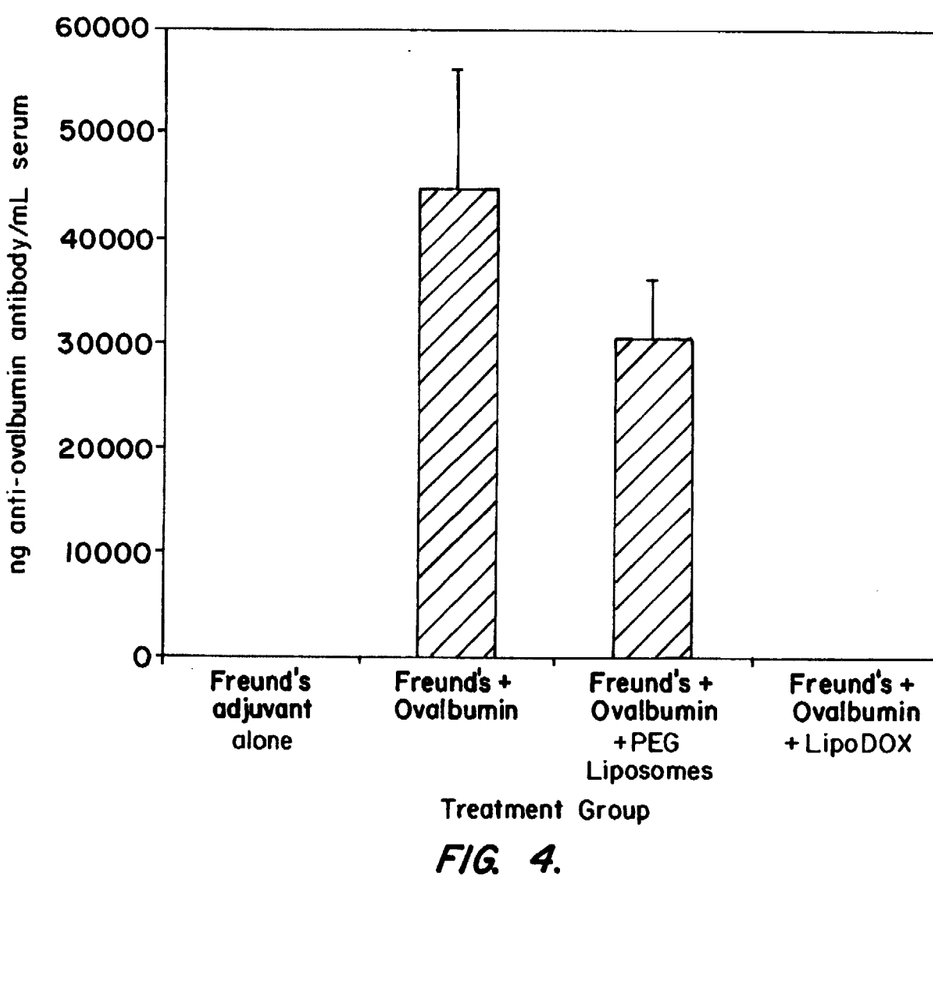
FIG. 4 shows an immune response to Freund's adjuvant. One week after the third weekly injection, the presence of antibodies against ovalbumin was determined by ELISA. The quantitation of antibody was achieved by comparing against values generated by a commercially available anti-ovalbumin antibody. The results are plotted as an average of four separate experiments.

It can be suggested that the immunization achieved through i.v. administration of ovalbumin-coated PEG liposomes is not optimal in terms of eliciting an immune response. In order to determine whether liposomal doxorubicin is capable of inhibiting generation of anti-ovalbumin antibodies under more stringent conditions, animals were immunized with free ovalbumin mixed with Freund's adjuvant (see Methods). Briefly, animals were given three weekly i.p. injections of Freund's adjuvant plus ovalbumin (50 mg/mouse) and the level of circulating anti-ovalbumin IgG was determined one week after the last injection. Four hours prior to each i.p. injection of Freund's adjuvant/ ovalbumin mixture, animals were given an i.v. injection of saline, control liposomes (DSPC/Chol (55:45; mol/mol)) or liposomal doxorubicin (DSPC/Chol, 55:45; mol/mol with doxorubicin encapsulated to achieve a final drug-to-lipid ratio of 0.2 mol/mol). The results, shown in FIG. 4, clearly demonstrate that production of anti-ovalbumin IgG after immunizing animals with ovalbumin mixed with Freund's adjuvant is prevented when the animals are pre-treated, prior to immunization, with liposomal doxorubicin. It is interesting to note that the anti-ovalbumin antibody levels achieved following i.p injection of protein mixed with Freund's adjuvant is only about 5-fold greater than that observed with i.v. injections of ovalbumin-coated PEG liposomes.

EXAMPLE 4

This example illustrates the influence of anti-ovalbumin IgG on plasma clearance rates for ovalbumin-coated PEG liposomes.

Figure 3:
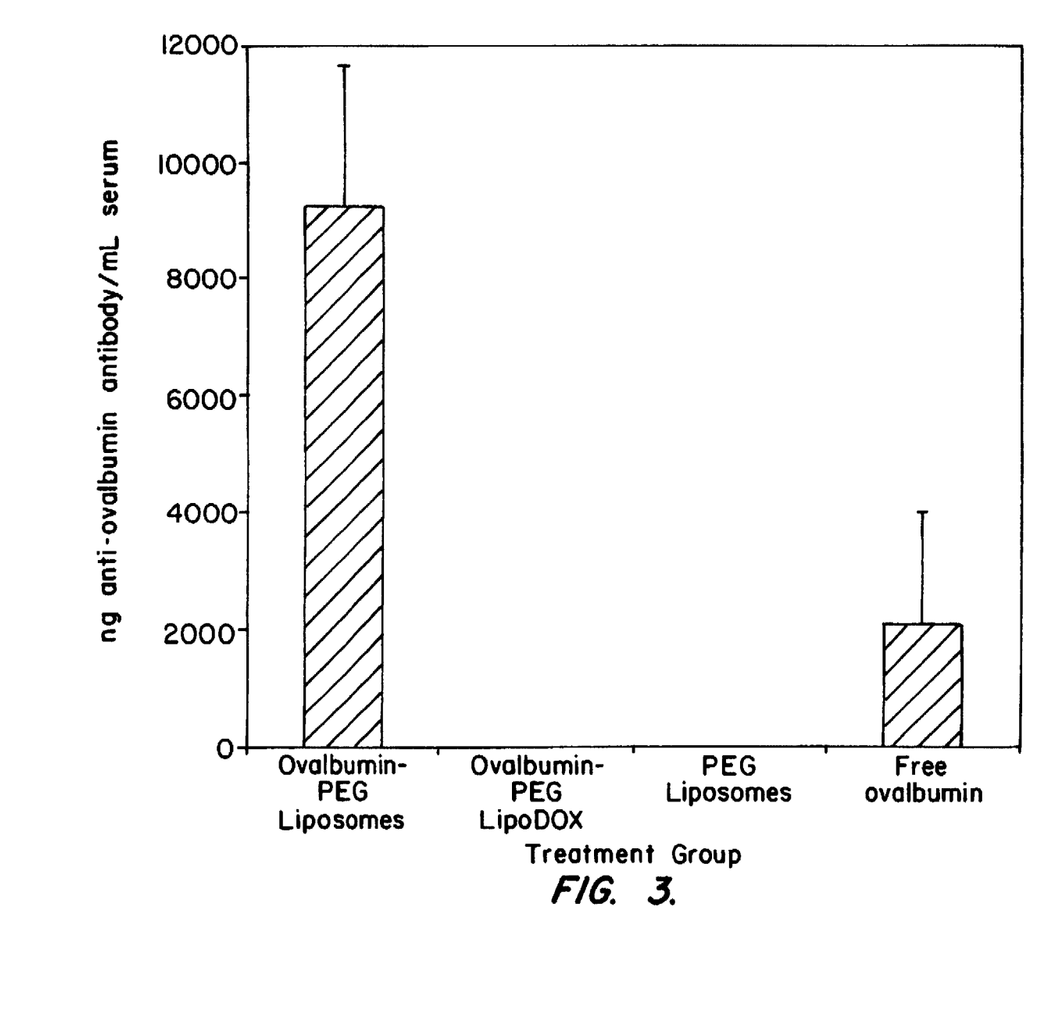
FIG. 3 shows the production of anti-ovalbumin antibodies. One week after the third weekly injection, the presence of antibodies against ovalbumin was determined by ELISA. The quantitation of antibody was achieved by comparing against values generated by a commercially available anti-ovalbumin antibody. The results are plotted as an average of four separate experiments.
Figure 5:
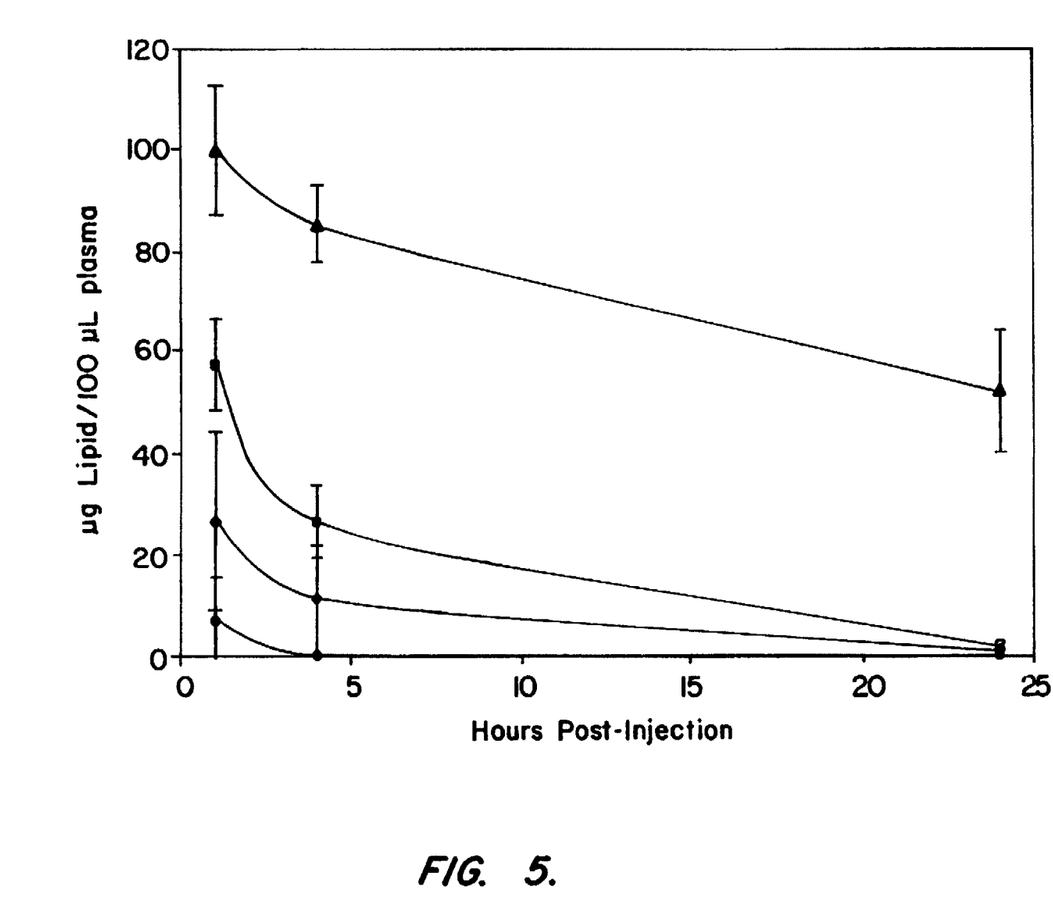
FIG. 5 shows the clearance of ovalbumin-coated PEG liposomes. Mice were injected (i.v.) for three consecutive weeks with either free ovalbumin (♦), 2% PEG liposomes (■), ovalbumin-coated 2% PEG liposomes (●) or ovalbumin-coated, doxorubicin loaded 2% PEG liposomes (▲). On the fourth week, all mice were injected i.v. with ovalbumin-coated 2% PEG liposomes. Clearance of the fourth dose was monitored by collecting blood at various time points and the amount of lipid remaining in the blood determined. The results are plotted as an average of four separate experiments.

As suggested by the results shown in FIGS. 1 and 2 and elsewhere (see Harasym, et al., *Bioconjugate Chem.* 6:187 (1995)), a significant problem associated with therapeutic applications involving the use of protein coated liposomal carriers, will be decreases in carrier circulation longevity after repeated administration. The plasma clearance curves shown in FIG. 5 better illustrate this problem and how it can be avoided when the protein-coated liposomes contain doxorubicin. The data in FIG. 5 was obtained after each group was injected i.v. with ovalbumin-coated PEG liposomes at a lipid dose of 45 mg/kg. The groups differed in terms of previous treatment with three weekly i.v. injections of control liposomes, free ovalbumin, ovalbumin-coated PEG liposomes or doxorubicin-loaded ovalbumin-coated PEG liposomes. As indicated in FIG. 3, animals given weekly injections of free ovalbumin and ovalbumin-coated PEG liposomes will have measurable levels of anti-ovalbumin antibodies in the plasma. Plasma clearance of ovalbumin-coated PEG liposomes was most rapid in animals previously given ovalbumin-coated PEG liposomes and free ovalbumin. One hour after injection, less than 10% and 30% of the respective injected ovalbumin-coated PEG liposome dose was recovered from the plasma compartment. Plasma clearance of ovalbumin-coated PEG liposomes was unaffected by previous administration of control liposomes. The circulation half-life observed for these liposomes, approximately 1.5 hrs, was similar to that observed in animals that received no prior treatment (see FIG. 1). As anticipated from results shown in FIGS. 2 and 3, the circulation half-life of the ovalbumin-coated PEG liposomes was significantly greater in animals that had received three prior injections of doxorubicin-loaded ovalbumin-coated PEG liposomes. The estimated circulation half-life increased from 1.5 hrs in control animals to greater than 24 hrs.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method of increasing the circulation half-life of a protein-based therapeutic in a host, said method comprising:
   (a) administering to said host an amount of a first formulation comprising liposomes and an antineoplastic agent; and
   (b) administering to said host a second formulation comprising said protein-based therapeutic, wherein said amount of said first formulation is sufficient to suppress an IgG response to said protein-based therapeutic of said second formulation, thereby suppressing said IgG response and increasing the circulation half-life of said protein-based therapeutic, wherein said protein-based therapeutic is selected from the group consisting of protein-coated liposomes peptide-containing liposomes, therapeutic agents which are proteins or polypeptides, antibody-toxin conjugates, transferrin DNA bound to polylysine, and prodrugs having a protein-targeting group.

2. A method in accordance with claim 1, wherein said antineoplastic agent is a member selected from the group consisting of doxorubicin, vincristine, methotrexate, ciprofloxacin and cyclophosphamide.

3. A method in accordance with claim 1, wherein said antineoplastic agent is doxorubicin.

4. A method in accordance with claim 1, wherein said first formulation comprises liposomes encapsulating doxorubicin.

5. A method in accordance with claim 1, wherein said protein-based therapeutics are antibody-coated liposomes.

6. A method in accordance with claim 1, wherein said protein-based therapeutics are viral protein-coated liposomes.

7. A method in accordance with claim 1, wherein said protein-based therapeutics are drug carriers.

8. A method in accordance with claim 5, wherein said antibody-coated liposomes are prepared using N-succinimidyl 3-(2-pyridyldithio) propionic acid as a linking group to attach said antibody to said liposome.

9. A method in accordance with claim 8, wherein said antibody is specific for an antigen on a cancer cell.

10. A method in accordance with claim 1, wherein said first formulation and said second formulation are administered simultaneously.

11. A method in accordance with claim 1, wherein said first formulation is administered prior to said second formulation.

12. A method in accordance with claim 1, wherein said host is a member selected from the group consisting of human, rat, mouse, dog, cow, sheep, horse, cat and goat.

13. A method in accordance with claim 1, wherein said host is human.

14. A method in accordance with claim 1, wherein said second formulation further comprises an encapsulated therapeutic agent.

* * * * *